(12) United States Patent
Danenberg et al.

(10) Patent No.: US 8,257,742 B2
(45) Date of Patent: Sep. 4, 2012

(54) BISPHOSPHONATES FOR TREATING ENDOMETRIOSIS

(75) Inventors: Haim Danenberg, Jerusalem (IL); Morey Schachter, Mazkeret Batia (IL); Gershon Golomb, Efrat (IL)

(73) Assignees: Yissum Research Development Company of the Hebrew University of Jerusalem (IL); Hadasit Medical Research Services & Development Ltd. (IL)

( * ) Notice: Subject to any disclaimer, the term of this patent is extended or adjusted under 35 U.S.C. 154(b) by 568 days.

(21) Appl. No.: 11/816,245

(22) PCT Filed: Feb. 16, 2006

(86) PCT No.: PCT/IL2006/000209
§ 371 (c)(1),
(2), (4) Date: Nov. 24, 2008

(87) PCT Pub. No.: WO2006/087722
PCT Pub. Date: Aug. 24, 2006

(65) Prior Publication Data
US 2009/0238876 A1 Sep. 24, 2009

Related U.S. Application Data
(60) Provisional application No. 60/653,526, filed on Feb. 17, 2005.

(51) Int. Cl.
A61K 9/14 (2006.01)
A61K 9/16 (2006.01)
(52) U.S. Cl. .......................... 424/489; 424/490
(58) Field of Classification Search .................. None
See application file for complete search history.

(56) References Cited

U.S. PATENT DOCUMENTS

| | | | |
|---|---|---|---|
| 5,681,817 A * | 10/1997 | Hodgen et al. | 514/10.3 |
| 5,877,284 A | 3/1999 | Lyttle | |
| 6,121,230 A | 9/2000 | Charnock-Jones et al. | |
| 6,346,534 B1 | 2/2002 | Zhu et al. | |
| 6,719,998 B1 * | 4/2004 | Golomb et al. | 424/450 |
| 2003/0064965 A1 * | 4/2003 | Richter | 514/102 |
| 2003/0118637 A1 * | 6/2003 | Jordan et al. | 424/450 |
| 2003/0157179 A1 * | 8/2003 | Blum et al. | 424/489 |
| 2003/0225132 A1 * | 12/2003 | DiNinno et al. | 514/321 |
| 2004/0005345 A1 * | 1/2004 | Pauletti et al. | 424/423 |
| 2004/0147484 A1 * | 7/2004 | Boyd et al. | 514/75 |
| 2004/0223971 A1 * | 11/2004 | Chang et al. | 424/155.1 |
| 2004/0266734 A1 * | 12/2004 | Danenberg et al. | 514/89 |
| 2005/0008633 A1 * | 1/2005 | Vanbever et al. | 424/130.1 |

FOREIGN PATENT DOCUMENTS

| | | |
|---|---|---|
| CA | 2 459 434 | 2/2003 |
| JP | H7-53593 | 2/1995 |
| WO | WO 9940787 A1 * | 8/1999 |
| WO | WO 03075741 A2 * | 9/2003 |
| WO | WO 03088950 A1 * | 10/2003 |
| WO | WO 2004/073610 | 9/2004 |
| WO | WO 2004073610 A2 * | 9/2004 |
| WO | WO 2005/002545 A1 | 1/2005 |

OTHER PUBLICATIONS

Takayama, Kazuto, et al., "Treatment of severe postmenopausal endometriosis with an aromatase inhibitor," Fertility and Sterility, 69(4): 709-713 (1998).
Schachter, M., et al., "Periotneal macrophage depiction by liposomal bisphosphonate inhibits implant growth in a rat model—a novel approach to endometriosis immunotherapy," European Journal of Obstertics & Gynecology and Reproductive Biology, 123:S58 (2005).
McLaren, et al., "Vascular Endothelial Growth Factor is Produced by Peritoneal Fluid Macrophages in Endometriosis and is Regulated by Ovarian Steroids," J. Clin. Invest., 98(2): 482-489 (Jul. 1996).
Matsuo, Hiroya—"Bone Loss Induced by GnRHa Treatment in Women," Nippon Rinsho, vol. 61, No. 2, p. 314-318, 2003.
Van Rooijen et al., "Elimination of Phagocytic Cells in the Spleen after Intravenous Injection of Liposome-Encapsulated Dichloromethylene Diphosphonate: An Enzyme-Histochemical Study" Cell and Tissue Research (1984) 239: pp. 355-358.
Takayama et al. "Treatment of Severe Postmenopausal Endometriosis With an Aromatase Inhibitor", *Fertility and Sterility*, vol. 69, No. 4, Apr. 1998.
Schachter et al. "124 Peritoneal Macrophage Depletion by Liposomal Bisphosphonate Inhibits Implant Growth in a Rat Model—a Novel Approach to Endometriosis Immunotherapy", *European Journal of Obstetrics & Gynecology and Reproductive Biology*, vol. 123, p. S58, Sep. 2005.
International Search Report for Corresponding PCT Application PCT/IL2006/000209 dated (mailing date) May 18, 2006.
Written Opinion for Corresponding PCT Application PCT/IL2006/000209 dated (mailing date) May 18, 2006.
McLaren, et al., "Vascular Endothelial Growth Factor is Produced by Peritoneal Fluid Macrophages in Endometriosis and Is Regulated by Ovarian Steroids," J. Clin. Invest., vol. 98, No. 2, Jul. 1996, pp. 482-489.

* cited by examiner

*Primary Examiner* — Robert A Wax
*Assistant Examiner* — Olga V Tcherkasskaya
(74) *Attorney, Agent, or Firm* — Cadwalader Wickersham & Taft LLP

(57) ABSTRACT

A novel method of treating endometriosis is disclosed. The method comprises administering to a female subject in need thereof a therapeutically effective amount of particles comprising an agent capable of inhibiting phagocytic cells of the female subject.

25 Claims, 5 Drawing Sheets

BISPHOSPHONATES FOR TREATING ENDOMETRIOSIS

CROSS-REFERENCE TO RELATED APPLICATIONS

This application is an national stage application under 35 USC §371 of International Application No. PCT/IL2006/000209, filed Feb. 16, 2006, which claims the benefit of U.S. Application No. 60/653,526, filed on Feb. 17, 2005.

FIELD AND BACKGROUND OF THE INVENTION

The present invention relates to a method of treating endometriosis and, more particularly, to particles comprising an agent capable of inhibiting phagocytic cells.

Endometriosis (EM) is a gynecological disorder characterized by growth of tissue resembling endometrium outside of the uterine cavity. Its major clinical components include pelvic pain, dysmenorrhea, dyspareunia, pelvic/abdominal masses and infertility. Intra-abdominal bleeding episodes incite local inflammatory processes which lead to adhesion formation and ongoing intraperitoneal immunological dysfunction, which serves to aggravate both the pain and infertility involved in active EM.

Endometriosis affects 5-10% of reproductive age women. The prevalence of endometriosis in infertile women has been found to be as high as 62%, in teenagers with severe dysmenorrhea to be 50%, and in asymptomatic women undergoing laparoscopy for tubal ligation to be 4%.

Current clinical protocols dictate that surgical laparoscopy is the gold standard by which endometriosis is diagnosed and treated. Thus 20,000-40,000 patients needing laparoscopies for endometriosis are being seen every year in the US alone. Young patients can expect a recurrence rate of 30-60% within one year of follow-up, or in the over-all endometriosis population, 5-20% per year, with a cumulative recurrence rate for 5 years of 40%. The rate of recurrence increases with the initial staging, duration of follow-up and is associated with previous surgery. Conventional medical treatment can postpone recurrence, but not prevent it. These treatments include oral contraceptives, gonadotropin releasing hormone and danazol. Symptoms (pain or infertility) will recur in 20% of women with documented "complete" surgical resection within 5 years. Effective primary prevention is not possible at this time, as no specific markers of women at risk have been clearly identified.

Thus there is an urgent need for agents capable of preventing the occurrence of endometriosis, eliminating the lesions once diagnosed, and preventing recurrence.

The immunobiology of endometriosis is extremely complex and as yet not fully understood. Initial implantation necessitates mechanisms allowing attachment and persistence of endometrial cells to peritoneal surfaces, which probably include induction of reduced natural killer activity and evasion from immunosurveillance by production of blocking antibodies in the form of soluble ICAM-1. Endometrial cells also elaborate increased amounts of various cytokines, including monocyte activators such as RANTES and MCP-1. Activation of macrophages and peritoneal inflammation is central to the initiation, implantation and perpetuation of EM. Activated macrophages perpetuate the immune dysfunction by secreting lymphocyte activating factors, endometrial stromal proliferation and angiogenic factors and by encouraging EM cell growth and vascularization. Moreover, macrophage activation also interferes with fertility by elaborating IL-1β and TNFα which hinder uterine and embryonic function. The macrophage therefore is pivotal in initiating and maintaining endometriosis.

The TNF-α binding protein r-hTBP (currently in clinical use for rheumatoid arthritis and other inflammatory syndromes) was examined in a rat model and found, in small number of animals, to reduce the size of endometriotic lesions by 64%, and a recent report using the same preparation in a baboon model showed better results when hormone treatment was combined with TBP than with hormones alone. Regression of endometriosis explants was observed using another immuno-modulatory drug, loxoribine. Loxoribine is a guanine derivative with immuno-enhancing properties and increases lymphocytic Natural Killer activity. However, both these treatment regimes are not specific and might therefore induce unwanted side-effects. In addition, none of these studies have been substantiated in human clinical trials.

Bisphosphonates (BPs) are widely used in treating osteoporosis and other bone diseases. Although characterized by a very poor cell membrane permeability, BPs have a high affinity for bone mineral and once incorporated into bone tissue they may directly be internalized by monocyte-derived osteoclasts and ultimately inhibit them.

It has been found by the present inventors that phagocytic cells such as macrophages and monocytes may be depleted by particle-mediated intracellular delivery of BPs with minimal effect on smooth muscle and endothelial cells. The BPs inactivate and kill the macrophages and monocytes following effective phagocytosis. Thus, U.S. Pat. No. 6,719,998 to Golomb teaches particle enclosed bisphosphonates for the treatment of restenosis. In addition, U.S. Patent Application No. 20040266734 to Danenberg teaches particle enclosed bisphosphonates for the treatment of cardiac macrophage-associated inflammatory disorders such as unstable angina and myocardial infarction. The use of bisphosphonates, particles of bisphosphonates or particulated drugs in general for the treatment of endometriosis has never been suggested.

SUMMARY OF THE INVENTION

According to one aspect of the present invention there is provided a use of particles comprising an agent for inhibiting phagocytic cells for the manufacture of a medicament identified for treating endometriosis.

According to another aspect of the present invention there is provided a use of particles comprising a bisphosphonate for the manufacture of a medicament identified for treating endometriosis.

According to yet another aspect of the present invention there is provided a method of treating endometriosis, the method comprising administering to a female subject in need thereof a therapeutically effective amount of particles comprising an agent capable of inhibiting phagocytic cells of the female subject, thereby treating endometriosis.

According to still another aspect of the present invention there is provided a method of treating endometriosis, the method comprising administering to a female subject in need thereof a therapeutically effective amount of particles comprising bisphosphonate, thereby treating endometriosis.

According to further features in preferred embodiments of the invention described below, the agent is a bisphosphonate.

According to still further features in the described preferred embodiments, the phagocytic cells are macrophages or monocytes.

According to still further features in the described preferred embodiments, the inhibiting phagocytic cells is effected by eliminating, retarding the proliferation and/or down regulating the activity of the phagocytic cells.

According to still further features in the described preferred embodiments, the bisphosphonate comprises a compound having the following formula I:

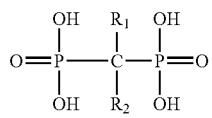

wherein $R_1$ is H, OH or a halogen atom and;

$R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino where the amino may be a primary, secondary or tertiary; —NHY where Y is hydrogen, $C_3$-$C_8$ cycloalkyl, aryl or heteroaryl; or $R_2$ is —SZ where Z is chlorosubstituted phenyl or pyridinyl.

According to still further features in the described preferred embodiments, the bisphosphonate is selected from the group consisting of clodronate, etidronate, tiludronate, pamidronate, neridronate, olipadronate, alendronate, ibandronate, risendronate and zoledronate.

According to still further features in the described preferred embodiments, the particles are selected from the group consisting of polymeric particles, microcapsules liposomes, microspheres, microemulsions, nanoparticles, nanocapsules and nanospheres.

According to still further features in the described preferred embodiments, the particles are between 0.02 and 1 micron in size.

According to still further features in the described preferred embodiments, the particles comprising an agent are selected from the group consisting of aggregates, flocculates, colloids, polymer chains, insoluble salts and insoluble complexes.

According to still further features in the described preferred embodiments, the particles comprising bisphosphonate are selected from the group consisting of aggregates, flocculates, colloids, polymer chains, insoluble salts and insoluble complexes.

According to still further features in the described preferred embodiments, the agent is encapsulated within the particle.

According to still further features in the described preferred embodiments, the bisphosphonate is encapsulated within the particle.

According to still further features in the described preferred embodiments, the agent is embedded within the particle.

According to still further features in the described preferred embodiments, the bisphosphonate is embedded within the particle.

According to still further features in the described preferred embodiments, the agent is adsorbed on the particle surface.

According to still further features in the described preferred embodiments, the bisphosphonate is adsorbed on the particle surface.

According to still further features in the described preferred embodiments, the particles are adapted for intraperitonal administration.

According to still further features in the described preferred embodiments, the particles are adapted for intravenous administration.

According to still further features in the described preferred embodiments, the particles further comprise an immune suppressor agent.

According to still further features in the described preferred embodiments, the treating comprises preventing the recurrence of said endometriosis.

According to still further features in the described preferred embodiments, the method further comprises administering a hormone prior to, concomitant with and/or following administering the particles.

According to still further features in the described preferred embodiments, the hormone is selected from the group consisting of a contraceptive, gonadotropin releasing hormone and danazol.

According to still further features in the described preferred embodiments, the method further comprises administering an immune suppressor agent prior to, concomitant with and/or following administering the particles.

According to still further features in the described preferred embodiments, the immune suppressor agent is co-formulated in the particles.

According to still further features in the described preferred embodiments, the immune suppressor agent is r-hTBP or Loxoribine.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a novel use of particles containing agents capable of inhibiting phagocytic cells.

Specifically, the loaded particles may be used to treat endometriosis.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Endometriosis (EM) is the growth of endometrial tissue at a site outside of the uterus, usually the peritoneum. Intra-abdominal bleeding episodes incite local inflammatory processes which lead to adhesion formation and ongoing intra-peritoneal immunological dysfunction, which serves to aggravate both the pain and infertility involved in active EM.

Endometriosis is typically treated by surgical laparoscopy. However, the rate of recurrence is high and increases with the initial staging, duration of follow-up and association with previous surgery. Conventional medical treatment can postpone recurrence, but not prevent it. These treatments include oral contraceptives, gonadotropin releasing hormone and danazol.

The present inventors have previously found that phagocytic cells such as macrophages and monocytes may be depleted by particle-mediated intracellular delivery of bisphosphonates (BPs) with minimal effect on smooth muscle and endothelial cells. The BPs inactivate and kill the macrophages and monocytes following effective phagocytosis. Thus, U.S. Pat. No. 6,719,998 to Golomb teaches particle enclosed bisphosphonates for the treatment of restenosis. In addition, U.S. Patent Application No. 20040266734 to Danenberg teaches particle enclosed bisphosphonates for the treatment of cardiac associated inflammatory disorders such as unstable angina and myocardial infarction.

While reducing the present invention to practice, the inventors uncovered that particles including agents for inhibiting phagocytic cells may also be used to treat endometriosis.

Figure 4:
FIG. 4 is a photomicrograph of a typical endometriotic implant resected 4 weeks following initial endometriosis-inducing surgery, treated by 1 mg/kg/week liposome enclosed alendorate. Paraffin sections were stained with Hematoxylin-Eosin and counterstained with ED1 rat anti-macrophage antibodies. Magnification ×400.
Figure 5:
FIG. 5 is a photomicrograph of a typical endometriotic implant resected 4 weeks following initial endometriosis-inducing surgery, treated by placebo. Paraffin sections were stained with Hematoxylin-Eosin and counterstained with ED1 rat anti-macrophage antibodies. Magnification ×400.

As is illustrated herein below and in the Examples section which follows, administration of liposome-loaded bisphosphonate to an endometriosis rat model resulted in a reduced endometriosis implantation rate, a reduced endometriosis mean diameter, a reduced endometriosis mean volume and reduced endometriosis adhesion. Immunohistochemistry demonstrated a significantly reduced pattern of macrophage infiltration following liposome-loaded bisphosphonate treatment (FIGS. 4 and 5).

Thus, according to one aspect of the present invention, there is provided a method of treating endometriosis comprising administering to a female subject in need thereof a therapeutically effective amount of particles including an agent capable of inhibiting phagocytic cells of the female subject, thereby treating endometriosis.

Herein, the term "treating" includes abrogating, substantially inhibiting, slowing or reversing the progression of endometriosis or substantially preventing the onset of endometriosis or symptoms of endometriosis or preventing recurrence of endometriosis after conventional treatment, in particular for preventing recurrence after surgical intervention. Preferably, treating cures, e.g., substantially eliminates, the symptoms associated with endometriosis.

As used herein, the term "endometriosis" also termed as adenomyosis externa and exdometriosis externa refers to a disorder in which an endometrial tissue is present in a location in the body other than the uterus, i.e. outside the uterine cavity (e.g., pelvic cavity) or is present within the myometrium of the uterus such as uterosacral nodules, endometriomas, adnexal adhesions, and adenomyosis. Endometriosis also includes adenomyoma, endometriotic or adenomyotic nodules of the uterosacral ligaments and endometriotic nodules elsewhere such as scar endometriosis.

The term "subject" as used herein, refers to a female mammal, preferably a human female subject of any age. Preferably the female subject does not suffer from, and is not treated for a disease selected from: restenosis, cardiac macrophage associated inflammatory disorders such as unstable angina and myocardial infraction.

As used herein, the phrase "phagocytic cells" are cells which are capable of phagocytosis. The term phagocytosis also encompasses forms of endocytosis, including but not limited to pinocytosis, receptor-mediated endocytosis and other cellular means for absorbing/internalizing material from outside the immune cells of the present invention.

Examples of phagocytic cells include, but are not limited to cells of the mononuclear phagocytic system, (MPS), including, but not limited to macrophages and circulating monocytes. Other cells capable of phagocytosis include for example neutrophils, dendritic cells, and fibroblasts. Most preferably the phagocytic cells are macrophages and/or monocytes.

According to this aspect of the present invention, inhibition of phagocytic cells includes reducing the number of, eliminating (i.e., killing), retarding the proliferation of and/or reducing the activity of phagocytic cells (e.g. reducing the ability to phagocytose or to secrete cytokines). Pharmaceutical agents capable of inhibiting phagocytic cells are described herein below.

As used herein the term "particle" refers to fully closed carrier molecules including but not limited to polymeric particles, microcapsules liposomes, microspheres, microemulsions, nanoparticles, nanocapsules and nonospheres.

According to this aspect of the present invention, particles are prepared so that the size of the particle is large enough to only, or primarily be, internalized by phagocytosis, thus imparting preferred selectivity to phagocytic cells. Particles of the present invention of less than 1.0 μm are typically used to avoid side effects (such as disruption of the BBB, blockage of the lungs, blockage of alveolar and pulmonary blood vessels, and complement activation).

Particles imparting extrinsic specificity to macrophages are preferably in the size range of 0.02-1.0 microns, more preferably 0.08-0.5 microns and more preferably 0.08-0.3 microns.

Any method known in the art can be used to determine the size of the particle before administration to a patient in need thereof. For example, a Nicomp Submicron Particle Sizer (model 370, Nicomp, Santa Barbara, Calif.) utilizing laser light scattering can be used. Other methods of sizing particles are detailed herein below.

Determination of the optimal size, formulation and/or amount, of a particle to be engulfed by a phagocytic cell may be determined using procedures known in the art such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106:599-605; Circulation 2003, 108:2798-804. For example, particles may be formulated such that they contain fluorescent markers such as the hydrophilic marker 1-Hydroxypyren-3,6,8-Trisulfonic acid and the hydrophobic marker Rhodamin-DSPE. In an in vitro screening assay, liposome uptake is examined on tissue culture of macrophages. The phagocytic cells may be obtained from an established cell line or recently isolated from an individual as a primary cell line. In an in vivo assay, particles can be administered to a test subject (e.g. mouse, rabbit) and after a set amount of time tissues may be removed and examined using confocal microscopy. The tissue may be stained for mitochondrial markers, such as those used in the Examples section below to ascertain whether the fluorescent marker co-stains with the mitochondrial marker.

Typically, particles of the present invention sequester the agents capable of inhibiting phagocytic cells for a sufficient time to enhance delivery of the agent to the target site. Furthermore, the agent is typically released from the particles when they are within the target cell (e.g., the phagocytic cell) at the target site.

In one embodiment, the agent capable of inhibiting phagocytic cells is encapsulated in a carrier (i.e., encapsulating agent) of desired properties. In a specific embodiment, the encapsulating agent is a liposome. As used herein and as recognized in the art, liposomes include any synthetic (i.e., not naturally occurring) structure composed of lipids in a liquid crystalline phase or a liquid gel phase, which enclose a liquid volume.

Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral or, more preferably, negatively charged. It is also preferable that the liposomes are hydrophobic since hydrophilic masking of the liposome membrane (e.g., by use of polyetheleneglycol-linked lipids and hydrophilic particles) may be less prone to MPS uptake. It is also preferable that the liposomes do not comprise sterically shielded lipids such as ganglioside-$GM_1$ and phosphatidylinositol since these lipids prevent MPS uptake. Since inclusion of cholesterol in the liposome enhances uptake by the MPS [Ahsan, F. et al., 2002, Journal of controlled Release, 79, 29-40], the lipsosomes of the present invention may also include cholesterol.

As detailed above, many properties influence uptake of liposomes by phagocytic cells including, but not limited to liposome size, charge and hydrophobicity, as well as the phospholipids and non-phospholipid components of the liposome.

The liposomes may be modified in any other way to enhance their uptake by the phagocytic cells, e.g. by attaching to them molecules recognized selectively by phagocytic cells such as ligands that interact with the macrophage Fc receptor, or galactosyl ligands, or inclusion of substances in the bilayer such as complement fibronectin lipoproteins or gamma globulin.

The liposomes may be a single lipid layer or may be multilamellar. If the agent capable of inhibiting phagocytic cells is hydrophilic, its delivery may be further improved using large unilamellar vesicles because of their greater internal volume. Conversely, if the agent is hydrophobic, its delivery may be further improved using multilamellar vesicles. Alternatively, the agent capable of down-regulating phagocytic cells (e.g. oligonucleotide) may not be able to penetrate the lipid bilayer and consequently would remain adsorbed to the liposome surface. In this case, increasing the surface area of the liposome may further improve delivery of the therapeutic agent. Suitable liposomes in accordance with the invention are preferably non-toxic liposomes such as, for example, those prepared from phosphatidyl-choline phosphoglycerol, and cholesterol. The diameter of the liposomes used preferably ranges from 0.08-1.0 microns. However, other size ranges suitable for phagocytosis by phagocytic cells may also be used. For sizing liposomes, homogenization may be used, which relies on shearing energy to fragment large liposomes into smaller ones. Homogenizers which may be conveniently used include microfluidizers produced by Microfluidics of Boston, Mass. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

In another embodiment, the agent capable of inhibiting phagocytic cells is embedded in a carrier (i.e., embedding agent) of desired properties. An agent which is embedded includes those agents that are embedded, enclosed, and/or adsorbed within a carrier, dispersed in the carrier matrix, adsorbed or linked on the carrier surface, or a combination of any of these forms. In specific embodiments, the embedding agent (or carrier) is a microparticle, nanoparticle, nanosphere, microsphere, microcapsule, or nanocapsule [Nanoparticle Technology for Drug Delivery, R B Gupta, Taylor & Francis, 2006; and Pharmaceutical Emulsions and Suspensions, F. Nielloud, CRC, 2000]. The term carrier includes both polymeric and non-polymeric preparations.

According to a specific embodiment, the embedding agent is a nanoparticle. Preferably, nanoparticles are 0.03-1.0 microns in diameter and can be spherical, non-spherical, or polymeric particles. The agent capable of inhibiting phagocytic cells may be embedded in the nanoparticle, dispersed uniformly or non-uniformly in the polymer matrix, adsorbed on the surface, or in combination of any of these forms. In a preferred embodiment, the polymer used for fabricating nanoparticles is biocompatible and biodegradable, such as poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

The present invention also envisages an agent capable of inhibiting phagocytic cells which is partially encapsulated within a particle and partially adsorbed on a particle.

In another embodiment, the agent capable of inhibiting phagocytic cells is formulated in particulate form, the particles each being of desired properties. A particulate agent form includes any insoluble suspended or dispersed particulate form of the agent which is not encapsulated, entrapped or absorbed within a carrier. An agent which is in particulate form includes those agents that are suspended or dispersed colloids, aggregates, flocculates, insoluble salts, insoluble complexes, and polymeric chains of an agent. Such particulates are insoluble in the fluid in which they are stored/administered (e.g., saline or water) as well as the fluid in which they provide their therapeutic effect (e.g., blood or serum). Typically, "insoluble" refers to a solubility of one (1) part of a particulate therapeutic agent in more than ten-thousand (10,000) parts of a solvent. Any method known in the art to make particulates or aggregates can be used. Preferably, particulates are 0.03-1.0 microns in diameter and can be any particular shape.

As mentioned herein above the particles used in the methods of the present invention preferably target phagocytic cells by virtue of the physiochemical properties, such as size or charge, of the carrier particle/formulation. The agents used in the methods of the present invention inhibit phagocytic cells by virtue of their biological properties. Once phagocytosed and intracellular, the agents of the present invention inhibit or decrease the activity of the phagocytic cell and/or destroy the phagocytic cell. Without being bound to theory, the agents of the formulation are released upon becoming intracellular before disabling and/or destroying the phagocytic cell.

The agent may be an intra-cellular inhibitor, deactivator, toxin, arresting substance and/or cytostatic/cytotoxic substance that, once inside a phagocytic cell such as a macrophage or monocyte, inhibits, destroys, arrests, modifies and/or alters the phagocytic cell such that it can no longer function normally and/or survive.

Examples of agents that inhibit phagocytic cells include, but are not limited to, inorganic or organic compounds; small molecules (less than 500 Daltons) or large molecules; proteinaceous molecules, including, but not limited to, peptide, polypeptide, protein, post-translationally modified proteins and antibodies; or nucleic acid molecules, including, but not limited to, double-stranded DNA, single-stranded DNA, double-stranded RNA, single-stranded RNA, or triple helix nucleic acid molecules. Agents can be natural products derived from any known organism (including, but not limited to, animals, plants, bacteria, fingi, protista, or viruses) or from a library of synthetic molecules. Therapeutic agents can be monomeric as well as polymeric compounds.

According to a preferred embodiment of this aspect of the present invention, the agent is a bisphosphonate or analog thereof.

The term "bisphosphonate" as used herein, denotes both geminal and non-geminal bisphosphonates. In a specific embodiment, the bisphosphonate has the following formula (I):

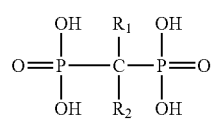

wherein $R_1$ is H, OH or a halogen atom; and $R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino where the amino may be a primary, secondary or tertiary; —NHY where Y is hydrogen, $C_3$-$C_8$ cycloalkyl, aryl or heteroaryl; or $R_2$ is —SZ where Z is chlorosubstituted phenyl or pyridinyl.

In a more specific embodiment, the bisphosphonate is alendronate or an analog thereof. In such an embodiment, the alendronate has the following formula (II):

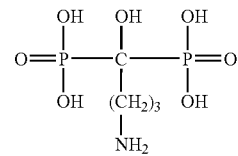

In other specific embodiments, additional bisphosphonates can be used in the methods of the invention. Examples of other bisphosphonates include, but are not limited to, clodronate, tiludronate, pamidronate, neridronate, olipadronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-di-phosphonic acid, e.g. amino-hexyl-BP; 3-(N-methyl-N-pentylamino)-1-hydroxy-propane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydrox-ypropane-1,1-bishosphonic acid; 1-hydroxy-3-(pyrrolidin-1-yl)propane-1,1-b-isphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-dip-hosphonic acid tetraethyl ester, e.g. U81581 (Upjohn); and 1-hydroxy-2-(imidazo[1,2-a]pyridin-3-yl)ethane-1,1-diphosphonic acid, e.g. YM 529, or analogs thereof.

It is envisaged that the particles of the present invention comprise more than one agent capable of inhibiting phagocytic cells such as those described herein above. Furthermore in accordance with the invention, a mixed population of particles, (two or more different populations) each comprising a different active agent, may be used.

In addition, the particles of the present invention may be used to treat endometriosis in combination with another therapy, such as hormone therapy an immunosuppressant or an anti-inflammatory agent (i.e., combination therapy), whereby, the above particles are administered prior to, concomitant with of following the other treating modality (e.g., hormone therapy). Examples of hormone treatments which may be used to treat endometriosis in combination with the particles of the present invention include but are not limited to oral contraceptives, such as a combination of oestrogen and progesterone, Gn-RH agonists (gonadotropin releasing hormone), progestin or danazol. Examples of anti-inflammatory agent which may be used to treat endometriosis in combination with the particles of the present invention include anti-prostaglandins such as aspirin or ibuprofen. Examples of immunosuppressant agents include, but are not limited to r-hTBP and Loxoribine.

The agent-loaded particles of the present invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent capable of inhibiting phagocytic cells which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

The concentration of particles in these formulations can vary widely, i.e., from less than about 0.5%, usually at or at least about it to as much as 15 or 20% by weight and will be selected primarily by fluid volumes, viscosities, etc., in accordance with the particular mode of administration selected. Actual methods for preparing particle formulations will be known or apparent to those skilled in the art and are described in detail in, for example, Remington's Pharmaceutical Science, Mack Publishing company, Easton, Pa., latest edition.

Any route of administration may be taken provided that the particles are in contact with phagocytic cells (e.g. circulating monocytes or peritoneal macrophages) in the area of endometriosis. For example, suitable routes of administration include parenteral delivery, including intramuscular, subcutaneous injections as well as direct intraventricular, intravenous, intra-arterial, intraperitoneal and intranasal injections.

As mentioned herein above, the particles of the present invention may be administered systemically (e.g. intravenously) so as to reduce circulating monocytes and thus limit the number of functional macrophages in the endometrium.

In order to selectively down-regulate phagocytic cells in the endometriosis area, a particularly preferred route of administration is intraperitoneally. For example, the particles of the present invention may be administered via direct intraperitoneal injection. Alternatively, the particles of the present invention may be administered during a laparoscopic or laparotomic surgery. If the laparoscopic or laparotomic surgery is performed to remove the endometriosis, the particles are typically administered so as to prevent recurrence following surgery. The particles may be administered prior to or following removal of the endometriosis. For a laparoscopy, the abdomen is inflated with gas, typically carbon dioxide. The gas, which is injected with a specialized needle, pushes the abdominal wall away from the organs. A laparoscope is then inserted through a small incision and the particles may be administered into the peritoneal cavity and/or injected into the lesions under direct vision.

Yet alternatively, the particles of the present invention may be administered directly into the endometriosis (intralesionally) via laparoscope or ultrasound-guided injection during a procedure to reduce/remove an endometriosis or an in-vitro-fertilization (IVF) procedure.

Still alternatively, the particles of the present invention may be administered into the peritoneum via a device similar to those configured for peritoneal dialysis. For example, the particles may be administered via an indwelling peritoneal catheter which is typically inserted surgically during a laparotomy or laparoscopically. Fibrous tissue attaches to the catheter's polyester fabric cuffs, anchoring the catheter subcutaneously and sealing the peritoneal cavity from bacteria tracking in from the skin and from leakage. The catheter typically remains in the body for a limited time e.g. 30-120 days. Although peritoneal dialysis catheters can be used immediately after insertion, a 10- to 14-day waiting period is recommended to promote healing and decrease the chance of leaks.

Still alternatively, administering intraperitoneally may be effected by installation through the uterine cavity and fallopian tubes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen, and the agent.

For injection, the active ingredients of the pharmaceutical composition may be formulated in aqueous solutions, preferably in physiologically compatible buffers such as amino acid buffers e.g. histidine buffers.

The pharmaceutical composition described herein is preferably formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles (such as sesame oil, or synthetic fatty acids esters such as ethyl oleate, triglycerides), and may contain formulatory agents such as suspending, stabilizing and/or dispersing agents.

Aqueous injection suspensions may contain substances, which increase the viscosity of the suspension, such as sodium carboxymethyl cellulose, sorbitol or dextran.

Alternatively, the active ingredient may be in powder form for constitution with a suitable vehicle, e.g., sterile, pyrogen-free water based solution, before use.

Pharmaceutical compositions suitable for use in context of the present invention include compositions wherein the active ingredients are contained in an amount effective to achieve the intended purpose. More specifically, a therapeutically effective amount means an amount of active ingredients (therapeutic drug) effective to prevent, alleviate or ameliorate symptoms of a disorder (e.g., streptococcal pharyngitis) or prolong the survival of the subject being treated. A diagnostically effective amount is an amount of active ingredients (diagnostic agent) that allows diagnosis of a disorder (including the presence, stage or treatment regime required).

Determination of a therapeutically and diagnostically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See for example, "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Liposome enclosed alendorate was tested in a rat model for the treatment of endometriosis.

Materials and Methods

Development of endometriosis in a rat model: 24 adult female Sabra strain rats were subjected to an endometriosis model, by resection of one uterine horn. The uterine horn was removed under anesthesia by ligation of the uterine horn at the uterotubal and cervical end and immersed in a sterile solution. The endometrium was exposed by cutting lengthwise with a scalpel, and six squares of opened uterine horn were cut and sutured onto the mesentery of the small intestine by 5/0 nylon sutures.

Liposome Preparation: Liposome enclosed alendronate, was prepared by thin lipid film hydration. DSPC, DSPG, and Cholesterol (3:1:2) were dissolved in t-butanol and lyophilized over night. The lyophilized cake was hydrated with an aqueous solution containing alendronate (CIPLA LTD, Mahesh Hiremath, Mumbai-400 008, INDIA) at 55-60° C. and left to stand for 1 hour at the same temperature. The suspension was then extruded three times through double polycarbonate membranes of 0.8, 0.4, and 0.2 μm pore sizes (Nucleopore), by means of an extruder. Liposomes were passed through a Sephadex G-50 column and eluted in MES/HEPES buffer pH 7.2 (50 mM MES, 50 mM HEPES, 75 mM NaCl) to remove un-encapsulated drug.

Animal treatment: The rats were divided randomly into two treatment and one control group, and treated with 4 weekly intraperitonal injections of liposome enclosed alendronate. Two treatment doses were employed, 1 mg/kg per injection and 10 mg/kg per injection. Four weeks following the initial surgery, the rats were sacrificed.

Specimen preparation and analysis: The number and size of implants were recorded, implantation rate calculated (i.e. number of implants on sacrifice/number of implants induced) and adhesions were graded by a 1-10 scoring, by a blinded observer.

Tissue sections of the implants were fixed in formalin and embedded in paraffin. Tissue slices were cut and fixed on slides. The slides were stained with hematoxylin-eosin. The tissues were stained with mouse anti-rat macrophage antigen ED1 (CD68. Serotec, UK) and counter-stained with goat anti-mouse Ig-biotin (Jackson ImmunoResearch). The slides were then scored blind by two observers and the density of macrophage infiltration in one implant per rat was scored by counting stained macrophages in a High Power Field, and averaging scores of 5 fields per case. The score was expressed as the average number of stained macrophages counted per 800 background cells.

Results

Figure 1:
FIG. 1 is a photograph of intra-abdominal adhesions 4 weeks following initial endometriosis-inducing surgery in the rat model.
Figure 2:
FIG. 2 is a photograph of endometriotic cyst upon laparotomy 4 weeks following initial endometriosis-inducing surgery in the rat model.
Figure 3:
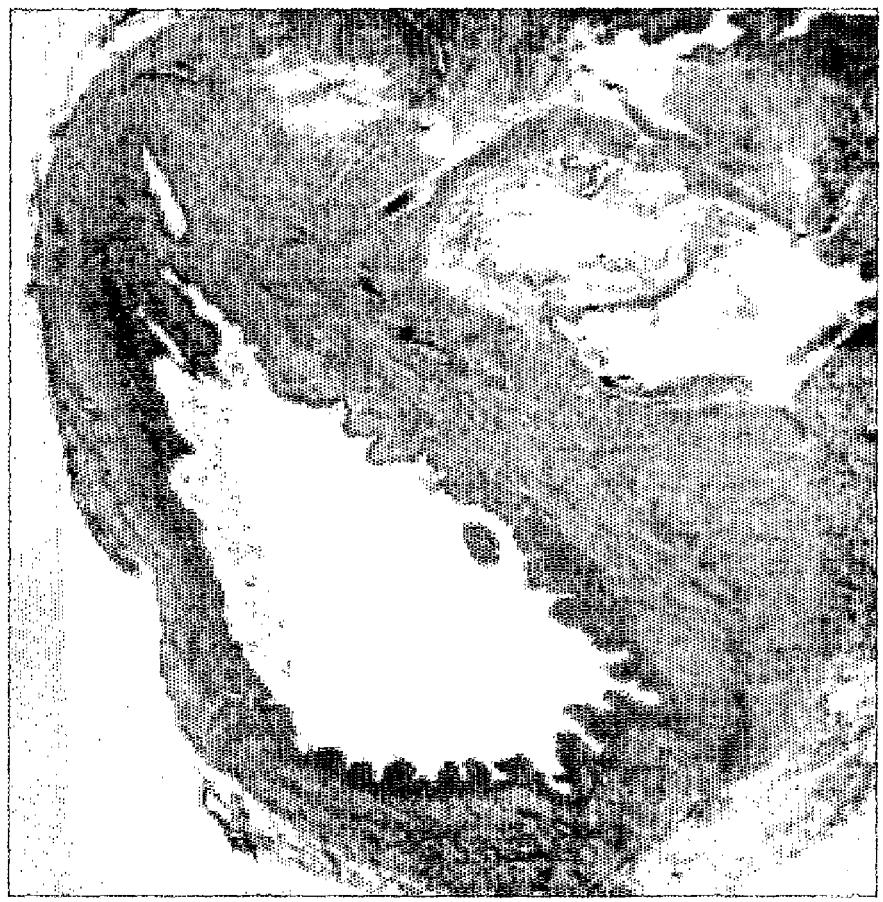
FIG. 3 is a photomicrograph of a typical endometriotic cyst stained with Hematoxylin-Eosin, resected 4 weeks following initial endometriosis-inducing surgery. Magnification ×400.

The endometriosis model was validated by the demonstration of a 97% implantation rate in the control group, with a mean adhesion score of 8.5/10; (FIG. 1). Macro-pathology demonstrated typical endometriosis cysts (FIG. 2). H&E staining revealed endometrial stroma and glands surrounding a cystic cavity—indicative of endometriosis (FIG. 3). Treatment with both low-dose and high-dose liposome enclosed alendorate significantly reduced the implantation rate, mean diameter, mean volume of the endometriosis implants and adhesion score (see Table 1 below). No significant differences were detected between the high and low dose groups, although adhesion scores were somewhat lower in the high-dose group. Immunohistochemistry demonstrated a significantly reduced pattern of macrophage infiltration in the low dose (1 mg/kg per injection) treatment as opposed to the control group. The alendorate treated rats showed a low density of stained cells (FIG. 4), whereas the placebo treated rats showed a high density of stained cells (FIG. 5).

No significant differences were found between the high dose (10 mg/kg/dose) and control group (see Table 1 below, FIGS. 4 and 5).

TABLE 1

|  | Control (n = 8) | Low dose liposome enclosed alendorate (n = 9) | High dose liposome enclosed alendorate (n = 7) |
| --- | --- | --- | --- |
| Implantation rate (%) | 45/48 (93.7%) | 47/54 (87%)* | 25/42 (59.5%)* |
| Mean diameter implant (mm) (± SD) | 4.9 (±2.4) | 3.2 (±2.2)* | 3.3 (±2.2)* |
| Adhesion Score (1-10 per animal) | 69/80 | 47/90* | 31/70* |
| Volume implants (log 10 volume [mm³]) | 1.64 (±0.63) | 1.03 (±0.88)* | 1.14 (±0.71)* |
| Macrophage immunohistology staining score (of 800) (±SD)** | 300 (±124) | 107 (±144) | 320 (±174) |

*$p < 0.02$ between control and either treatment group.
**$p = 0.02$ between Control and Low dose group but not High dose group.

CONCLUSION

Activated macrophages play a pivotal role in the initiation and proliferation of endometriosis implants. Macrophage depletion using intraperitoneal liposomal alendronate effectively inhibited the initiation and growth of endometriosis implants, in a rat endometriosis model.

It is appreciated that certain features of the invention, which are, for clarity, described in the context of separate embodiments, may also be provided in combination in a single embodiment. Conversely, various features of the invention, which, for brevity, are described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating endometriosis, the method comprising administering to a patient in need thereof a therapeutically effective amount of a formulation comprising particles containing a cytostatic agent wherein the particles have a size of 0.08 to 0.3 microns, wherein said particles inhibit phagocytic cells.

2. A method of treating endometriosis, the method comprising administering to a patient in need thereof a therapeutically effective amount of a formulation comprising particles containing a bisphosphonate wherein the particles have a size of 0.02 to 1.0 microns, wherein said particles inhibit phagocytic cells.

3. A method of treating endometriosis, the method comprising administering to a patient in need thereof a therapeutically effective amount of a formulation comprising particles containing a cytotoxic agent wherein the particles have a size of 0.08 to 0.3 microns, wherein said particles inhibit phagocytic cells.

4. The method of claims 1, 2 or 3 wherein said inhibiting phagocytic cells includes eliminating, retarding the proliferation and/or down regulating the activity of said phagocytic cells.

5. The method of claim 2, wherein said bisphosphonate comprises a compound having the following formula I:

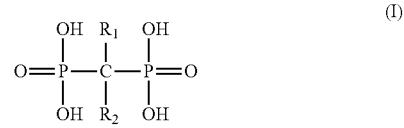

wherein $R_1$ is H, OH or halogen atom; and $R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino;

—NHY where Y is hydrogen, $C_3$-$C_8$ cycloalkyl, aryl or heteroaryl; or $R_2$ is —SZ where Z is chlorosubstituted phenyl or pyridinyl.

6. The method of claim 2, wherein said bisphosphonate is selected from the group consisting of clodronate, etidronate, tiludronate, pamidronate, neridronate, olpadronate, alendronate, ibandronate, risedronate and zoledronate.

7. The method of claims 1, 2 or 3, wherein said particles are selected from the group consisting of polymeric particles, microcapsules, liposomes, microspheres, microemulsions, nanoparticles, nanocapsules and nanospheres.

8. The method of claims 1 or 3, wherein said particles comprising an agent are selected from the group consisting of aggregates, flocculates, colloids, polymer chains, insoluble salts and insoluble complexes.

9. The method of claim 2, wherein said particles comprising bisphosphonate are selected from the group consisting of aggregates, flocculates, colloids, polymer chains, insoluble salts and insoluble complexes.

10. The method of claims 1 or 3, wherein said agent is encapsulated within said particle.

11. The method of claim 2, wherein said bisphosphonate is encapsulated within said particle.

12. The method of claims 1 or 3, wherein said agent is embedded within said particle.

13. The method of claim 2, wherein said bisphosphonate is embedded within said particle.

14. The method of claims 1 or 3, wherein said agent is adsorbed on said particle surface.

15. The method of claim 2, wherein said bisphosphonate is adsorbed on said particle surface.

16. The method of claims 1, 2 or 3, wherein said particles are adapted for intraperitonal administration.

17. The method of claims 1, 2 or 3, wherein said particles are adapted for intravenous administration.

18. The method of claims 1, 2 or 3, wherein said particles further comprise an immune suppressor agent.

19. The method of claims 1, 2 or 3, further comprising administering a hormone prior to, concomitant with and/or following administering said particles.

20. The method of claim 19, wherein said hormone is selected from the group consisting of a contraceptive, gonadotropin releasing hormone and danazol.

21. The method of claims 1, 2 or 3, further comprising administering an immune suppressor agent prior to, concomitant with and/or following administering said particles.

22. The method of claim 21, wherein said immune suppressor agent is co-formulated in said particles.

23. The method of claim 21, wherein said immune suppressor agent is r-hTBP.

24. The method of claims 1, 2 or 3, further comprising administering Loxoribine prior to, concomitant with and/or following administering said particles.

25. The method of claims 1, 2 or 3, wherein the phagocytic cells are macrophages or monocytes.

\* \* \* \* \*